US00PP12579P2

(12) United States Plant Patent
Meilland

(10) Patent No.: US PP12,579 P2
(45) Date of Patent: Apr. 23, 2002

(54) FLORIBUNDA ROSE PLANT NAMED 'MEIMONBLAN'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/649,216

(22) Filed: Aug. 28, 2000

(51) Int. Cl.[7] ..... A01H 5/00
(52) U.S. Cl. ..... Plt./146
(58) Field of Search ..... Plt./146

*Primary Examiner*—Bruce R. Campell
*Assistant Examiner*—Annette Para
(74) *Attorney, Agent, or Firm*—Burns, Doane, Swecker & Mathis, L.L.P.

(57) ABSTRACT

A new and distinct variety of Floribunda rose plant is provided which very abundantly forms on a remontant basis attractive Marigold Orange blossoms that are relatively stable in coloration. Such blossoms possess no fragrance. The plant exhibits a bushy growth habit, forms very dense medium green and glossy foliage, and possesses very good disease resistance. The new variety is particularly well suited for providing colorful ornamentation in the landscape.

1 Drawing Sheet

SUMMARY OF THE INVENTION

Figures 1, 2, 3, 4, 5, 6, 7, 8, 9, 10, 11, 12, 13, 14, 15, 16, 17:
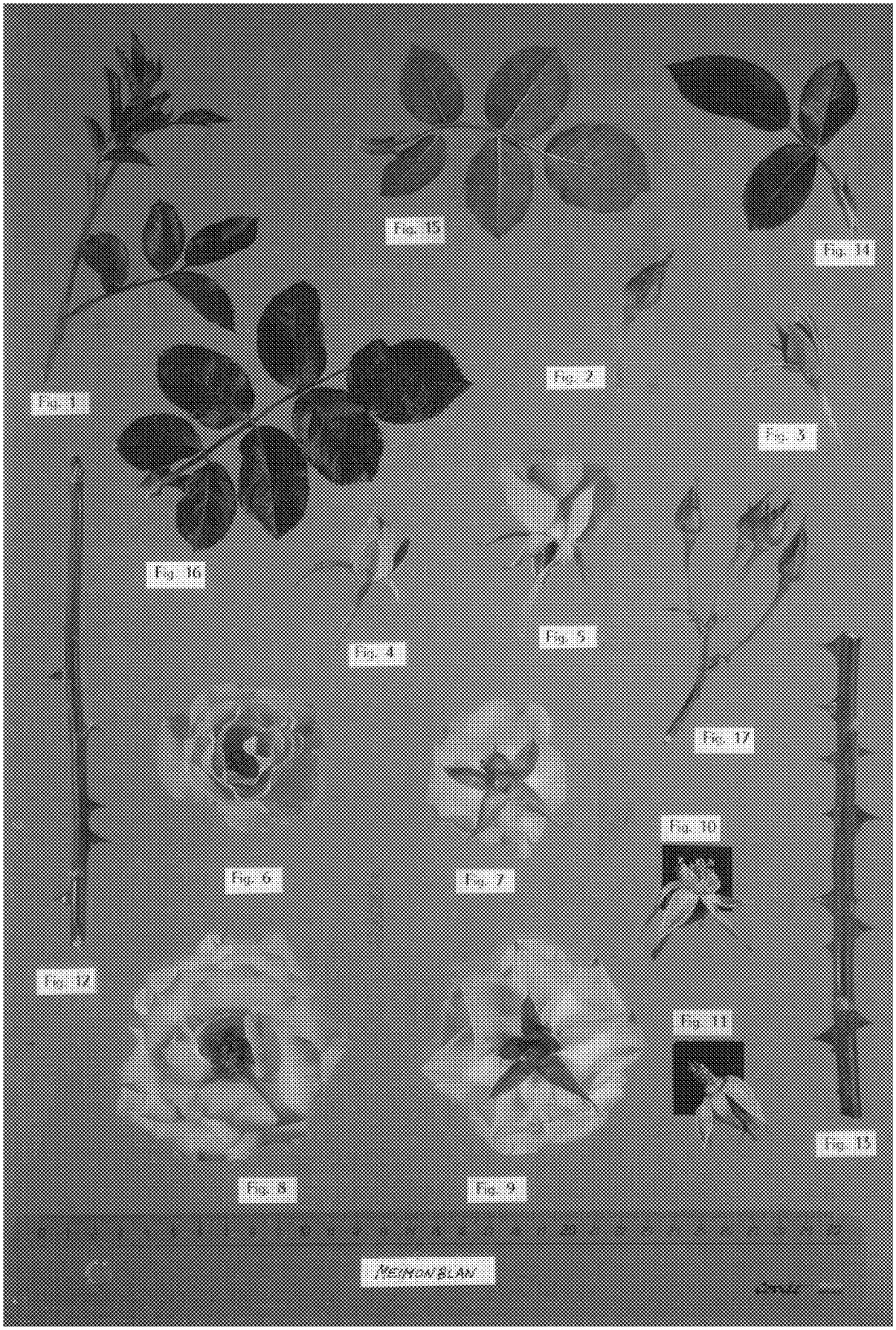

The new variety of Floribunda rose plant was created by artificial pollination wherein two parents were crossed whigh previously had been studied in the hope that they would contribute the desired characteristics. The female parent (i.e., the seed parent) of the new variety was the product of the cross of the 'Meidanu' variety (non-patented in the United States) and the 'Meichanso' variety (non-patented in the United States). The male parent (i.e., the pollen parent) was the 'Korpatri' variety (non-patented in the United States). The 'Meichanso' variety sometimes is known as the 'Parador' variety, and the 'Korpatri' variety sometimes is known as the 'Patricia' variety. The parentage of the new variety can be summarized as follows:

('Meidanu'×'Meichanso')×'Korpatri'.

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) Forms on a very abundant and remontant basis attractive double Marigold Orange blossoms that are relatively stable in coloration.
(b) Exhibits a bushy growth habit,
(c) Forms attractive very dense medium green glossy foliage, and
(d) Is particularly well suited for growing as ornamentation in parks and gardens.

The new variety of the present invention can be readily distinguished from its ancestors. For instance, the 'Meidanu' variety forms dark red blossoms while the new variety is shorter in stature and forms Marigold Orange blossoms. The 'Meichanso' variety forms larger blossoms that are geranium red in coloration. The 'Korpatri' variety exhibits a more erect growth habit and forms smaller blossoms.

The new variety well meets the needs of the horticultural industry and is particularly well suited for growing in the landscape.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meimonblan' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelli* understock and growing outdoors at Le Cannet des Maures, Var, France. Dimensions in centimeters are indicated at the bottom of the photograph.

FIG. 1—illustrates a specimen of a young shoot;

FIG. 2—illustrates a spacemen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface;

FIG. 16—illustrates a leaf with seven leaflets—plan view—upper surface; and

FIG. 17—illustrates a specimen of a cluster of buds.

DETAILED DESCRIPTION

The chart used in the identification of the colors is that of The Royal Horticultural Society (R.H.S. Colour Chart). The description is based on the observation of two year-old plants during June while budded on *Rosa froebelli* understock and growing outdoors at Le Cannet des Maures, Var, France. The coloration in common terms precedes reference to the chart in some instances.

Class: Floribunda.

Plant:

*Height.*—Approximately 65 to 75 cm on average at the end of the growing season.

*Habit.*—Bushy.

Branches:

*Color.*—Young stems: near Yellow-Green Group 144A. Adult wood: near Yellow-Green Group 146C.

*Thorns.*—Size: Large (as illustrated), and commonly measure approximately 0.8 to 1 cm in length on average on mature stems and approximately 0.6 to 0.8 cm in length on average on immature stems. Quantity: moderately numerous (as illustrated). Color: near Greyed-Orange Group 166B on young stems and adult wood. Shape: rather flat and elongated on upper surface and slightly concave on the under surface.

Leaves:

*Stipules.*—Adnate, pectinate, and rather broad.

*Petioles.*—Upper surface: non-glandular and near Yellow-Green Group 147A in coloration. Under surface: near Yellow-Green Group 147lB in coloration, and commonly without prickles.

*Leaflets.*—Number: 3, 5, and 7 (most often). Shape: elliptic with a cuspidate tip and an obtuse base. Size: approximately 4 to 5 cm in length on average, and approximately 3.5 cm in width on average. Serration: uniform finely serrate (as illustrated). Texture: smooth. General appearance: very dense, medium green, and glossy foliage. Color (young foliage): Upper surface: near Yellow-Green Group 146A and bordered with anthocyanin coloration, near Greyed-Red Group 178B. Under surface: near Yellow-Green Group 146B and widely suffused with anthocyanin coloration, near Greyed-Red Group 178B. Color (adult foliage): Upper surface: near Yellow-Green Group 147A. Under surface: near Yellow-Green Group 146B.

Inflorescence:

*Number of flowers.*—Usually 6 to 15 flowers per stem.

*Peduncle.*—Rigid, near Yellow-Green Group 144A in coloration, medium in size, and approximately 3.5 cm in length.

*Sepals.*—Upper surface: tomentose, and near Yellow-Green Group 148D in coloration. Under surface: near Yellow-Green Group 146D in coloration. Configuration: commonly with some weak extensions.

*Buds.*—Shape: conical. Size: large. Length: approximately 2.5 cm on average. Color upon opening: Upper surface: Marigold Orange, near Orange Group 28B and 28C. Under surface: lighter Marigold Orange, near Orange Group 28C and 28D.

*Flower.*—Shape: flat cup-shaped. Diameter: commonly approximately 9 to 10 cm on average. Color (when opening begins): Upper surface: Marigold Orange, near Orange Group 28B and 28C. Under surface: lighter Marigold Orange, near Orange Group 28C and 28D. Color (when blooming): Upper surface: Marigold Orange, near Orange Group 28C and lightly bordered with Persimmon Orange, Orange Group 28A. Under surface: near Orange Group 28D. Color (at end of opening): Upper surface: Marigold Orange, near Orange Group 28C and lightly bordered with Persimmon Orange, Orange Group 28D. Under surface: near Orange Group 28D. Sepals: approximately 2 to 2.4 cm in length on average and approximately 0.8 cm in width on average. Fragrance: none. Lasting quality: long, approximately 10 days on the plant. Petal shape: rounded base and a reflexed tip. Anthers: near Yellow-Orange Group 15A in coloration. Filaments: near Orange-Red Group 31A in coloration. Stigmas: near Green-Yellow Group 1C in coloration. Styles: near Red Group 47C in coloration. Receptacle: near Yellow-Green Group 144A in coloration, and in longitudinal section in the shape of a funnel. Hips: generally round in configuration, approximately 2 mm in diameter, and near Orange-Red Group 31A in coloration. Seeds: commonly approximately 14 to 15 seeds per hip on average, approximately 0.2 mm in size, and Yellow-Orange Group 18C in coloration.

Development:

*Vegetation.*—Strong.

*Blooming.*—Very abundant and remontant.

*Resistance to diseases.*—Very good with respect to Powdery Mildew.

*Resistance to cold.*—Has withstood a temperature of −10° C.

*Resistance to drought.*—If drought is prolonged some defoliation has been observed.

*Aptitude to bear fruit.*—Medium.

I claim:

1. A new and distinct variety of Floribunda rose plant characterized by the following combination of characteristics:

(a) Forms on a very abundant and remontant basis attractive double Marigold Orange blossoms that are relatively stable in coloration.

(b) Exhibits a bushy growth habit, (c) Forms attractive very dense medium green glossy foliage, and (d) Is particularly well suited for growing in parks and gardens;

substantially as herein shown and described.

* * * * *

Reinow Blair